United States Patent [19]
Gray

[11] Patent Number: 5,954,639
[45] Date of Patent: Sep. 21, 1999

[54] SURGICAL RETRACTOR

[75] Inventor: Bruce Nathaniel Gray, Claremont, Australia

[73] Assignee: Pine Ridge Holdings Pty Ltd., Perth, Australia

[21] Appl. No.: 09/194,328

[22] PCT Filed: May 27, 1997

[86] PCT No.: PCT/AU97/00335

§ 371 Date: Nov. 24, 1998

§ 102(e) Date: Nov. 24, 1998

[87] PCT Pub. No.: WO97/45059

PCT Pub. Date: Dec. 4, 1997

[30] Foreign Application Priority Data

May 27, 1996 [AU] Australia ................................. P00076
May 12, 1997 [AU] Australia ................................. P06749

[51] Int. Cl.[6] .................................................. A61B 17/02
[52] U.S. Cl. ............................................. 600/233; 600/231
[58] Field of Search .................................. 600/231, 233, 600/232, 227, 217

[56] References Cited

U.S. PATENT DOCUMENTS

| 1,400,616 | 12/1921 | McCroy et al. . |
| 1,839,726 | 1/1932 | Arnold .................................... 600/233 |
| 1,963,176 | 6/1934 | Morin ..................................... 600/233 |
| 3,129,706 | 4/1964 | Reynolds, Jr. .......................... 600/233 |
| 3,221,743 | 12/1965 | Thompson et al. .................... 600/233 |
| 3,858,578 | 1/1975 | Milo . |
| 3,970,075 | 7/1976 | Sindelar et al. ........................ 600/231 |
| 4,274,398 | 6/1981 | Scott, Jr. . |
| 4,337,762 | 7/1982 | Gauthier ................................. 600/233 |
| 4,616,632 | 10/1986 | Wigoda . |
| 4,617,916 | 10/1986 | LeVahn et al. ......................... 600/231 |
| 5,857,965 | 1/1999 | Rootman et al. ....................... 600/233 |
| 5,876,333 | 3/1999 | Bigliani et al. ......................... 600/231 |

FOREIGN PATENT DOCUMENTS

| 12990 | 4/1929 | Australia . |
| 1088710 | 4/1984 | U.S.S.R. ................................. 600/233 |
| 1206277 | 9/1970 | United Kingdom . |

*Primary Examiner*—Paul J. Hirsch
*Attorney, Agent, or Firm*—Needle & Rosenberg, P.C.

[57] ABSTRACT

The present invention provides a retractor assembly capable of supporting at least a tissue engaging member in a manner allowing self alignment of the member subject to the pull force of the tissue engaged by the member. The retractor assembly comprises: (i) a frame member which supports a support member; (ii) at least one tissue engaging member which possesses at least a mounting arrangement which is capable of releasably engaging the support member; and (iii) a locking member which is capable of releasably engaging the tissue engaging member with the frame member and the support member to hold the tissue engaging member(s) in a substantially immovable position.

17 Claims, 2 Drawing Sheets

SURGICAL RETRACTOR

This invention relates to a surgical retractor assembly and in particular to a table mounted surgical retractor which is capable of supporting multiple tissue engaging members in a manner allowing self alignment of the members subject to the pull of force of the tissue engaged by them.

Surgical exposure of internal organs and tissues in a patient is essential for surgeons to perform operative procedures. There are many different parts in the human body which may require exposure during surgical operations, the type of exposure required will vary with the type of operation being performed. Mechanical devices known as surgical retractors have been developed to assist in providing such exposure. The principle behind surgical retractors is to hold apart those tissues or organs that overlie the organ(s) of interest.

Many different surgical retractors have been developed to hold apart tissues and or organs. Most retractors consist of a rigid frame onto which are attached a series of retractor blades which can be held in various positions. These retractor blades are often held onto the frame with some form of fixing device such as a clamp. In one surgical retractor, known as the Bookwater retractor, the blades engage a rigid frame by a series of clips that slot onto the frame and which allow the position of the blades to be adjusted by a ratchet mechanism. In another example of a retractor, known as a Omnitract, the frame consists of a wishbone mechanism and the blades are connected to the frame by a series of locking (clamping) devices. In a third example of a retractor, known as the Turner Warrick retractor, the frame consists of a round or oval frame and detachable blades are slotted into the frame in fixed positions.

The principle problems associated with use of the above mentioned retractor assemblies relate to the means by which the retractor blades engage the retractor frame and the manner in which the blades are then fastened to that frame. When clamps are used to fasten the retractor blades there exists the problem that they are often difficult to adjust and often need to be done up tightly to prevent movement during operative procedures. This can cause significant difficulties in releasing a retractor blade, particularly when a retractor blade is being removed following post operative procedures. When a retractor blade is fixed to a retractor frame there is also limited movement available with respect to the position of the retractor blade, thus the retractor blade may not sit properly against the true line of force of the tissue. This may result in either the tissue dislodging from a retractor blade or movement of the tissue during an operative procedure. Further, the present retractor assemblies typically consist of many parts, making the problem of sterilisation difficult.

The present invention seeks to provide a retractor assembly which ameliorates and or overcomes the above mentioned problems.

The present invention provides a retractor assembly capable of supporting at least a tissue engaging member in a manner allowing self alignment of the member subject to the pull of force of the tissue engaged by the member, the retractor assembly comprising:

(i) a frame member which supports a support member;
(ii) at least a tissue engaging member which possess at least a mounting arrangement which is capable of releasably engaging the support member; and
(iii) a locking member which is capable of releasably engaging the tissue engaging member with the frame member and the support member to hold the tissue engaging member(s) in a substantially immovable position.

Preferably, the tissue engaging member and the support member, engage in a manner permitting pivotal movement of the tissue engaging member about the support. When the tissue engaging member is so engaged to the support member, it should be able to move subject to the pull of the tissue engaged by the tissue engaging member. Pivotal (eg up and down) movement of the retractor member(s) provides a means to ensure that the member(s) sits properly in the true line of resistance of the tissue. This minimises tissue dislodging from a tissue engaging member(s) or movement of the tissue during an operative procedure.

Any frame member capable of supporting a support member may be used in the present invention. The particular shape of the frame member will typically depend on the type of surgery for which the retractor is used. For example, the frame member may be circular, ellipsoid, semi-circular, rectangular, square or in a wishbone shape. Most preferably, the frame member is arranged so that the tissue engaging members are positioned opposite each other on the frame member.

The support member may be of any type which is capable of engaging at least a mounting arrangement and which is capable of aiding in and engaging a locking member. Preferably the support member is suspended above or below the frame member. Most preferably, the support member is offset from the frame member so that It lies above and anterior to the perimeter of the frame member. For example, the support member may be a rail suspended above the frame member by at least a bollard or pillar arrangement. Alternatively, it may be a series of elongate loops extending along the perimeter of the frame member.

If bollard(s) or pillar(s) are used to support the support member, the bollard(s) or pillar(s) are preferably attached to the frame member at an angle of between 1 and 90 degrees relative to the horizontal axis of the frame member, when in use. Most preferably, they are at an angle of between 30 and 70 degrees and desirably the angle is from 40 to 45 degrees, wherein the angle is determined from the horizontal axis of the frame member, when in use.

Any tissue engaging member possessing a mounting arrangement may be used in the present invention. In one form of the invention the tissue engaging member consists of a tissues engaging portion (eg a blade or tissue clasping arrangement) and a handle portion. Located along the handle, there is preferably provided a series of mounting arrangements, such as hooks or clasping mechanisms, which protrude from the handle and which provide a means for the tissue engaging member to engage the support member. Preferably, the mounting arrangements extend along the length of the handle, thereby providing a plurality of positions which may be used to engage the tissue engaging member to the support member. Most preferably the mounting arrangement is a series of hooks formed along the handle of the tissue engaging member. By engaging the tissue engaging member to the support member via such an arrangement, a surgeon can quickly and easily move the position of the tissue engaging member(s) during the operative procedure without having to release and tighten locking clamps etc. Other arrangements will, however, by known to those skilled in the art.

In use, it is an advantage for the retractor to pull apart the patient's tissue along the line of resistance of the tissue. This may be achieved by using a plurality of tissue engaging members mounted opposite each other on the support member.

To prevent tissue from collapsing over organs and thus obscuring a physicians view of the internal cavity of a patient on whom an operation is being carried out, the tissue engaging members(s) should be held in place by at least a locking member which is capable of releasably engaging the tissue engaging member with the frame member and the support member. Preferably, the locking member is adapted to force the tissue engaging member(s) in a vertical direction, upwards and away from a patient. Any locking member achieving this end may be used in the present invention.

In one form of the invention, the locking member is a wedge-shaped member which is adapted to engage at least the tissue engaging member and which is capable of holding the member in an immovable position when engaged to the support member. Most preferably, the wedge-shaped member is brought into contact with the frame member and the support member in a manner which holds the member in an immovable position. For example, the wedge-shaped member may be slotted between and then forced into the gap between the frame member and the support member. Preferably, the wedge-shaped member is serrated wherein the serrations provide a mechanism for engaging the wedge against a surface of the frame member and or the support member.

In a particularly preferred form of the invention the wedge-shaped member is adapted to elevate the tissue engaging member as it is forced between the frame member and the support member. This may be achieved by adapting the apex of the wedge-shaped member to abut against the handle of the tissue engaging member and thus drive it upwards as it is forced between the frame member and the support member.

In use, a tissue engaging member is preferably positioned to support tissue or an organ. It is then preferably pulled out and engaged to the support member via the mounting arrangement. In such an embodiment the tissue engaging member should be free to pivot on the support member. Thus, it will provide tension in the line of resistance of the tissue. The member can then be fixed in that position or may be elevated slightly above that position by engaging the locking member.

To stabilise the frame member above a patient during an operative procedure there may be provided one or more support assembly to which the frame member may be fastened. Any support assembly may be used in this respect. For example, the support assembly may consist of: (i) a fastening means such as a clamp which fixes to the operating table via the side rails on the table (ii) attached to which there is a substantially vertical extension support bar (iii) to which is attached a coupling means (iv) which joins a substantially horizontal elongate extension rod which is connected to the frame member via a second coupling member which is capable of swivelling up to 360 degrees in both the vertical and horizontal direction. Preferably, the second coupling member possess at least a means for fastening the movement of the coupling member. Thus, by adjusting the substantially vertical extension support bar and the substantially horizontal elongate extension rod a physician or assistant can control the position of the retractor over a patient. Further positional control of the retractor is facilitated by the swivel action of the second coupling member.

Surgical Operation on the liver and organs in the upper abdomen require additional exposure of the organs on the under side of the diaphragm. In order to obtain adequate exposure of the liver, tissue engaging members must be placed under the ribs and costal cartilage so that the direction of retraction is in an upwards and outwards direction. When the retractor assembly is used for such operative procedures the frame member is preferably connected to (either directly or via a substantially horizontal extension rod) and supported by at least two support members. Moreover, the frame member is preferably semi-circular. In this respect, there may be provided between the support member and the frame member at least one mechanism for varying and locking the angle of the frame member relative to the support member to account for the shape of the ribs and the sub-costal angle. In a highly preferred form of the invention each support assembly is adapted to engage each end of the semi-circular frame member. Thus, when two semi-circular frame members are brought together a circular arrangement may be created.

It will be understood that there may be modifications and changes to the present invention that will be apparent to one skilled in the art upon reading this specification. These modifications are to be encompassed in the scope of the present invention.

The present invention will now be described by way of example only with reference to the accompanied drawings in which.

Figure 1:
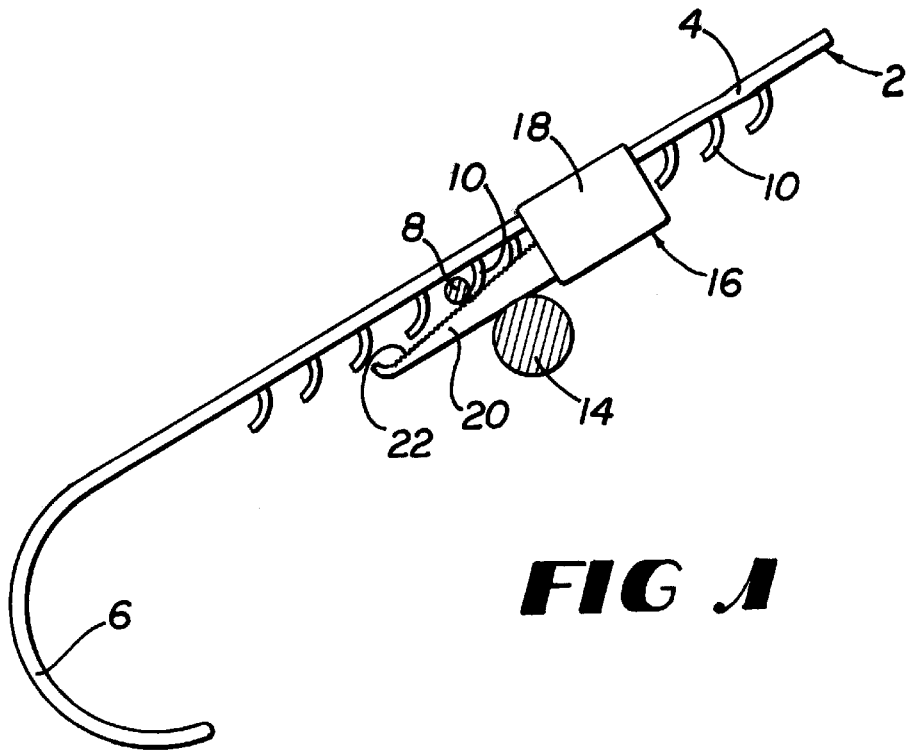
FIG. 1 illustrates the engagement between a frame member, a tissue engaging member and a locking means.

FIG. 1 illustrates a cross-section of a tissue engaging member 2 comprising a handle portion 4 and a blade portion 6 mounted to a support member 8 via a mounting arrangement (eg a hook) 10. Located along the handle portion 4 of the tissue engaging member 2 is a plurality of mounting arrangements in the shape of hooks 10 (generally) which are capable of releasably engaging the support member 8.

The support member 8 is suspended above and anterior to the frame member 14 via bollards or pillars (not shown). Positioned between the tissue engaging member 2 and the frame member 14 is a wedge-shaped locking member 16 which has a body portion 18 and a wedge-shaped portion 20. In use, the body portion 18 of the wedge-shaped locking member 16 is adapted to receive the handle portion 4 of the tissue engaging member 2. For example, the handle portion 4 may pass through a channel within the body portion. Alternatively, the body portion 18 may clip to the sides of the handle portion 4.

The wedge-shaped portion 20 engages mounting arrangement 10 at serrated surface 22 on the locking member 16. By driving the locking member 16 between the support 8 and the frame member 14 it is possible to fix the tissue engaging member 2 in a non-moveable arrangement relative to the frame member 14.

Figure 2B:
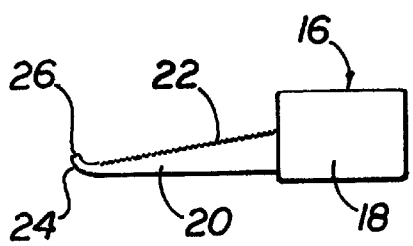
FIG. 2a, 2b, 2c illustrate locking means.
Figure 2A:
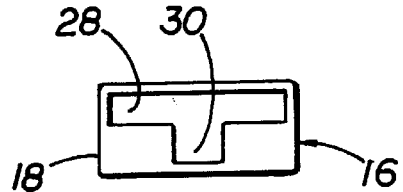
Figure 2C:
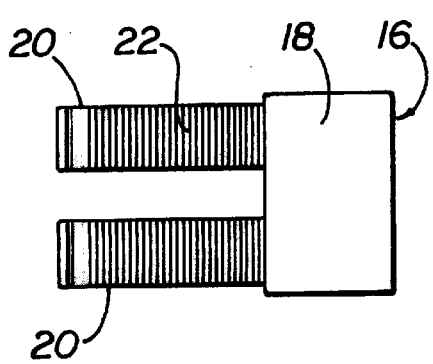

FIG. 2 illustrates a locking member 16 which may be used to hold the tissue engaging member to the frame member. The locking member consists of two wedge-shaped portions 20 attached to a body portion 18. At the apex 24 of each wedge-shaped portion is a tooth portion 26 which aids in driving the tissue engaging member in a vertical direction when in use. On the inclined surface of the wedge-shaped portion are serrations 22 which assist in engaging the tissue engaging member.

Passing through the body portion 18 is a passage 28 which is wide enough to receive the handle portion 4 of the wedge-shaped member and which contains a trough 30 through which the mounting arrangements 10 may pass when the wedge is brought into engagement with the tissue engaging member 2.

Figure 3:
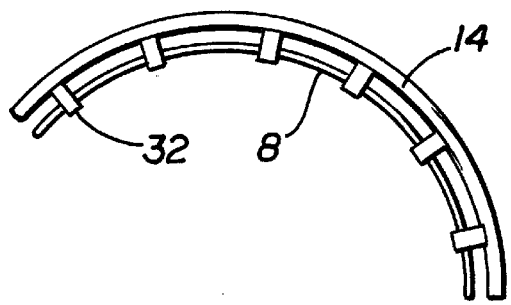
FIG. 3 illustrates the arrangement of bollards, a support member and a frame member.

FIG. 3 illustrates a frame member 14 possessing a plurality of bollards 32 supporting the support member 8 at an angle which is offset from the frame member 14 and which lies above and anterior to the frame member 14.

Figure 4A:
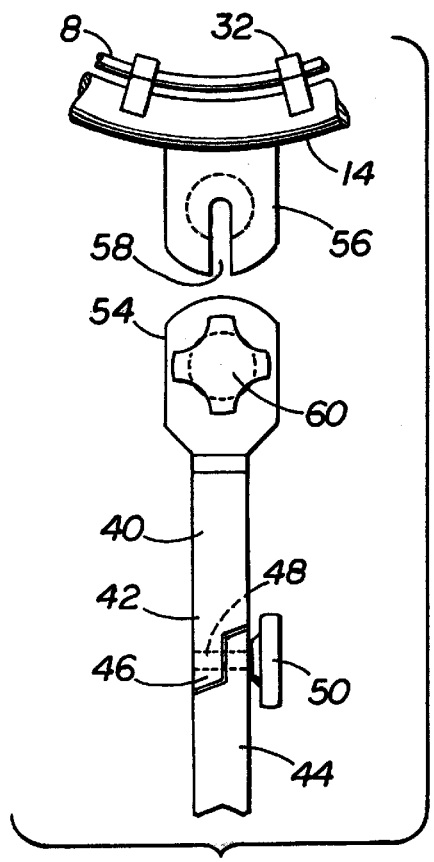
FIG. 4(a) illustrates one means by which a frame member may be fastened to a support member to allow rotation of the member.

FIG. 4a illustrates a frame member 14 in close proximity to a substantially horizontal elongate extension rod 40. The extension rod 40 consists of a frame member engaging portion 42 and an extension portion 44. The two portions join at angular adjustment means 46. In order to fasten the angular adjustment means there is provided a locking means 46. The locking means consists of a tightening knob 50 and a screw thread 48 which passes through the frame member engaging portion 42 and screws into the extension portion 44. In use, the frame member engaging portion 42 and the extension portion 44 are adjustable at the angular adjustment means 46 and are fastened via the locking means 46. At the end opposite to the angular adjustment means 46 on the frame member engaging portion 42 is a receiving means 54 for a frame member engaging member 56. Within the frame member engaging member 56 there is a slot 58 which is adapted to fit into the receiving means 54 and around locking member 60.

Figure 4B:
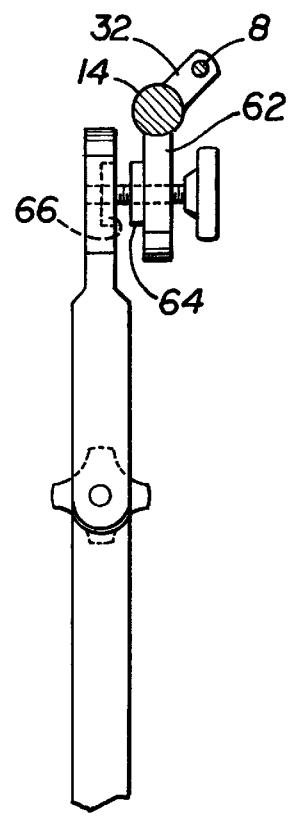
FIG. 4(b) illustrates the same means by which a frame member may be fastened to a support member, but the illustration is rotated 90 degrees relative to FIG. 4(a).

FIG. 4b illustrates the same structure as FIG. 4a, except that the extension rod has been turned 90° relative to the device shown in FIG. 4a. Further, the frame member engaging member 56 has been placed in releasable engagement with the receiving means 52. As illustrated in FIG. 4b the frame member engaging member 56 consists of a body portion 62 and a protruding portion 64 on the under side of the body portion 62. In use, the protruding portion 64 sits within a trough 66 located in the receiving means 52, the two members are then engaged via the locking member 60 which in this case is a screw which passes through the groove in the frame member engaging member and fastens to the extension rod within the trough 66.

Figure 5:
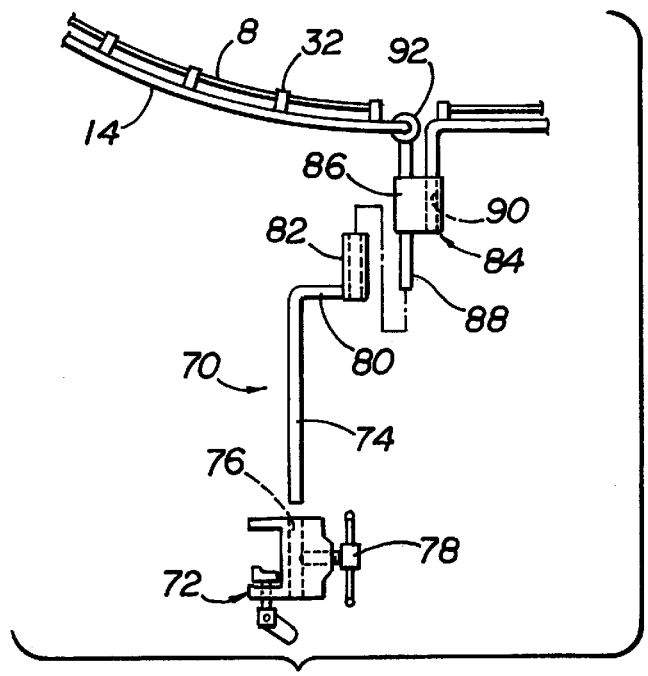
FIG. 5 illustrates a means by which a semi-circular frame member may be engaged to a support assembly capable of receiving a second frame member.

FIG. 5 illustrates a support assembly 70 consisting of a fastening means 72 such as a clamp which engages an operating table (not shown) and which is adapted to receive a support bar 74 via a recess in the fastening means 76. To prevent movement of the support bar 72 when located within the recess 76, there is provided a support bar fixing means 78 which consists of a screw which bites against the support bar therein locking it within the recess. At the end opposite of the attachment to the fastening means, the support bar 72 is bent 90 degrees to form a perpendicular projection 80 which terminates at a receiving tube 82 which extends substantially perpendicular to the perpendicular projection 80. The receiving tube 82 is adapted to receive an attachment member 84 which consists of a body portion 86, a rod portion 88 which is adapted to fit within the receiving tube 82, and one or more recesses 90 into which the frame member 14 may sit. To enable movement of the frame member, there is provided swivel 92 which permits adjustment of the angle of the frame member through an angle up to 360 degrees in both the vertical and horizontal direction.

The claims defining the invention are:

1. A retractor assembly capable of supporting at least one tissue engaging member in a manner allowing self alignment of the member subject to the pull of force of the tissue engaged by the member, the retractor assembly comprising:

(i) a frame member which supports a support member;

(ii) said at least one tissue engaging member which possesses at least a mounting arrangement which is capable of releasably engaging the support member; and (iii) a locking member which is capable of releasably engaging said at least one tissue engaging member with the frame member and the support member to hold the tissue engaging member in a substantially immovable position.

2. A retractor assembly according to claim 1 wherein said at least one tissue engaging member and the support member engage in a manner permitting pivotal movement of said at least one tissue engaging member about the support member.

3. A retractor assembly according to claim 1 wherein the frame member is circular, ellipsoid, semi-circular, rectangular, square or in a wishbone shape.

4. A retractor assembly according to claim 1 wherein the support member provides a means for engaging said mounting arrangement and which is capable of aiding in and engaging the locking member.

5. A retractor assembly according to claim 4 wherein the support member is suspended above and anterior to the perimeter of the frame member.

6. A retractor assembly according to claim 4 wherein the support member is suspended above the frame member by at least a bollard.

7. A retractor assembly according to claim 4 wherein the support member is suspended above the frame member by at least a series of elongated loops extending along the perimeter of the frame member.

8. A retractor assembly according to claim 1 wherein said at least one tissue engaging member consists of a tissues engaging portion and a handle portion.

9. A retractor assembly according to claim 1 wherein said at least one tissue engaging member possesses a series of mounting arrangements which protrude from the handle and which provide a means for said at least one tissue engaging member to engage the support member.

10. A retractor assembly according to claim 1 wherein said at least one tissue engaging member possesses a series of hooks which extend along the length of the handle providing a plurality of positions which may be used to engage said at least one tissue engaging member to the support member.

11. A retractor assembly according to claim 1 wherein said at least one tissue engaging member is held in place by said locking member which is capable of releasably engaging said at least one tissue engaging member with the frame member and the support member.

12. A retractor assembly according to claim 1 wherein the locking member is a wedge-shaped member which is adapted to engage at least said at least one tissue engaging member and which is capable of holding said at least one member in an immovable position when engaged to the support member.

13. A retractor assembly according to claim 1 wherein the locking member has serrations wherein the serrations provide a mechanism for engaging the locking member against a surface of the frame member and/or the support member.

14. A retractor assembly according to claim 1 wherein the locking member is adapted to elevate the tissue engaging member as it is forced between the frame member and the support member.

15. A retractor assembly according to claim 1 wherein the frame member is supported by at least a support assembly.

16. A retractor assembly according to claim 15 wherein the support assembly consists of:

(i) a fastening means which fixes to an operating table;

(ii) a substantially vertical extension support bar which attaches to the fastening means;

(iii) a coupling member which joins the vertical extension support bar to a substantially elongated extension rod which holds the retractor assembly; and (iv) said substantially elongated extension rod connecting the frame member via a second coupling member which is capable of swivelling up to 360 degrees in both the vertical and horizontal direction.

17. A retractor assembly according to claim 15 wherein the support assembly consists of two semi-circular frame members each of which engages said support assembly wherein each frame member is angled to account for the shape of the ribs and the sub-costal shape of the patient.

* * * * *